(12) United States Patent
Luo

(10) Patent No.: US 11,708,373 B2
(45) Date of Patent: Jul. 25, 2023

(54) 5-ALKYLQUINAZOLINE DERIVATIVE, METHOD OF PREPARING THE SAME, AND METHOD OF USING THE SAME

(71) Applicant: Hefei University of Technology, AnHui (CN)

(72) Inventor: Mei Luo, AnHui (CN)

(73) Assignee: HEFEI UNIVERSITY OF TECHNOLOGY, Anhui (CN)

( * ) Notice: Subject to any disclaimer, the term of this patent is extended or adjusted under 35 U.S.C. 154(b) by 0 days.

(21) Appl. No.: 17/488,847

(22) Filed: Sep. 29, 2021

(65) Prior Publication Data
US 2022/0185819 A1    Jun. 16, 2022

(30) Foreign Application Priority Data

Dec. 11, 2020  (CN) .......................... 202011453233.9

(51) Int. Cl.
  *C07D 487/10*  (2006.01)
  *A61P 35/00*  (2006.01)
(52) U.S. Cl.
  CPC ............ *C07D 487/10* (2013.01); *A61P 35/00* (2018.01)
(58) Field of Classification Search
  CPC ................................ C07D 487/10; A61P 35/00
  See application file for complete search history.

(56) References Cited

PUBLICATIONS

Structures of isamic acid and methylisatoid, J. of the Chem. Soc., Perkin Transactions 1: Organic and Bio-Organic Chemistry, (19) 2004-9 (1976). (Year: 1976).*

* cited by examiner

*Primary Examiner* — Erich A Leeser

(74) *Attorney, Agent, or Firm* — Muncy, Geissler, Olds & Lowe, P.C.

(57) ABSTRACT

A 5-methoxyquinazoline derivative compound I, having a structure represented by formula I:

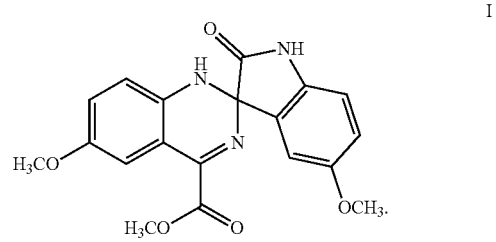

A 5-methylquinazoline derivative compound II, having a structure represented by formula II

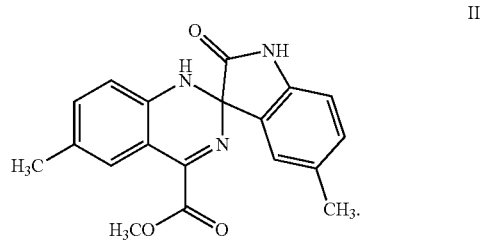

A method for preparing crystals of a 5-methoxyquinazoline derivative compound I and a 5-methylquinazoline derivative compound I, includes: adding 0.8847 g of 5-methoxyisatin, 0.8256 g of 5-methylisatin, 2.6963 g of ammonium formate, and 100 mL of anhydrous methanol in a 250 mL round-bottomed flask; heating and stirring a resulting mixture for refluxing for 48 hrs, stopping reaction, and performing rotary filtration and obtaining a crude filter residue; and performing column chromatography on the crude filter residue using dichloromethane and anhydrous methanol at a volume ratio of 1:1, and respectively obtaining the crystal of 5-methoxyquinazoline derivative compound I and the crystal of 5-methylquinazoline derivative compound II.

7 Claims, 1 Drawing Sheet

5-ALKYLQUINAZOLINE DERIVATIVE, METHOD OF PREPARING THE SAME, AND METHOD OF USING THE SAME

CROSS-REFERENCE TO RELATED APPLICATIONS

Pursuant to 35 U.S.C. § 119 and the Paris Convention Treaty, this application claims the benefit of Chinese Patent Application No. 202011453233.9 filed Dec. 11, 2020, the contents of which are incorporated herein by reference.

BACKGROUND

Technical Field

The present application relates to a new compound and use thereof, and more particular to a quinazoline and method of preparing the same, particularly to a 5-alkylquinazoline derivative and method of using the same.

Description of the Related Art

The statements herein only provide background information related to the present application, and do not necessarily constitute prior art.

A 5-alkylquinazoline derivative is a heterocyclic compound. The synthesis method thereof has been reported in similar literature [1]. However, the conventional synthesis method thereof involves multiple steps, which are complicate. Being a Lewis base, the 5-alkylquinazoline derivative can be developed as an organic catalyst and an anti-cancer reagent.

REFERENCE

1. Structures of isamic acid and methylisatoid, Journal of the Chemical Society, Perkin Transactions 1: Organic and Bio-Organic Chemistry (1972-1999) (1976), (19), 2004-9.

SUMMARY

In view of the above problems, it is one objective of the present application to provide a quinazoline derivate and a method for preparing the same, which aim at synthesizing the target product by one step.

The quinazoline as mentioned in the present application and the method for preparing the same involves a compound which is prepared by 5-methylisatin or 5-methoxyisatin and ammonium formate in an anhydrous methanol solution, and which has a structure presented by the following formula:

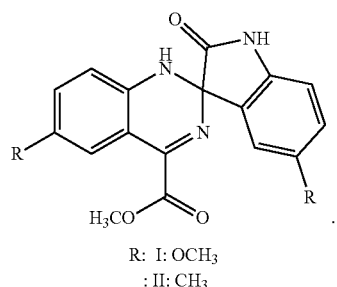

R: I: OCH$_3$
: II: CH$_3$

A chemical name of the structure presented by the above formula is 5,6'-di R group-2-oxo-1'H-spiro[indole-3,2'-quinazoline]-4'-carboxylic acid methyl ester, which is short for a compound I and a compound II. The compound I and the compound II have conversion rates of 90.7 wt. % and 89.0 wt. % in the Henry reaction of ethyl pyruvate, respectively. The compound II can be used as an anti-cancer agent, showing a certain anti-cancer effect in the anti-tumor cervical cancer activity.

The preparation method of the quinazoline derivate includes a synthesis step and a separation step. The synthesis step comprises: adding 0.8847 g of 5-methoxyisatin, 0.8256 g of 5-methylisatin, 2.6963 g of ammonium formate, and 100 mL of anhydrous methanol in a 250 mL round-bottomed flask; heating and stirring a resulting mixture for refluxing for 48 hrs, stopping reaction, and performing rotary filtration and obtaining a crude filter residue. The separation step comprises: performing column chromatography on the crude filter residue using dichloromethane and anhydrous methanol at a volume ratio of 1:1, and respectively obtaining the crystal of 5-methoxyquinazoline derivative compound I and the crystal of 5-methylquinazoline derivative compound II.

The synthesis reaction is shown as follows:

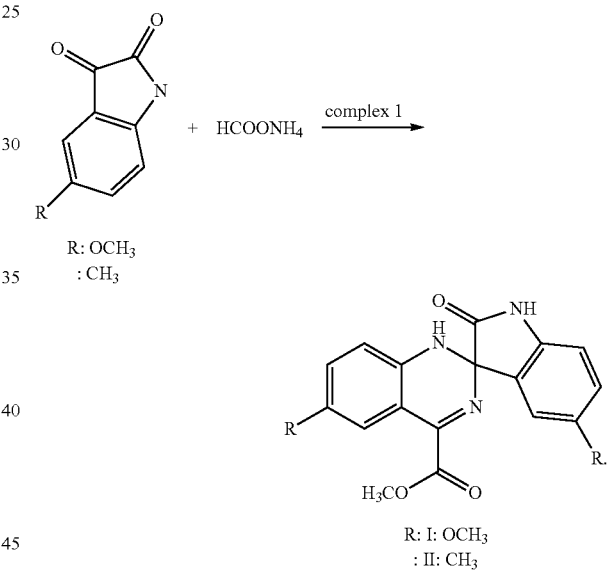

R: OCH$_3$
: CH$_3$

R: I: OCH$_3$
: II: CH$_3$

The synthesis method adopts one step reaction to obtain the target product, thus, the process is simple, and the operation is convenient.

The reaction mechanism of the synthesis reaction is complicated. The 5-alkyl-substituted isatin and ammonium formate react with each other in the presence of 1-2 mol % palladium complex in the methanol solution, during which, the carbonyl group reacts with ammonium formate and is converted into an amino group. After condensation and reaction with methanol, intermediate products are converted into compounds I and II in one step.

DETAILED DESCRIPTION OF THE EMBODIMENTS

Figure 1:
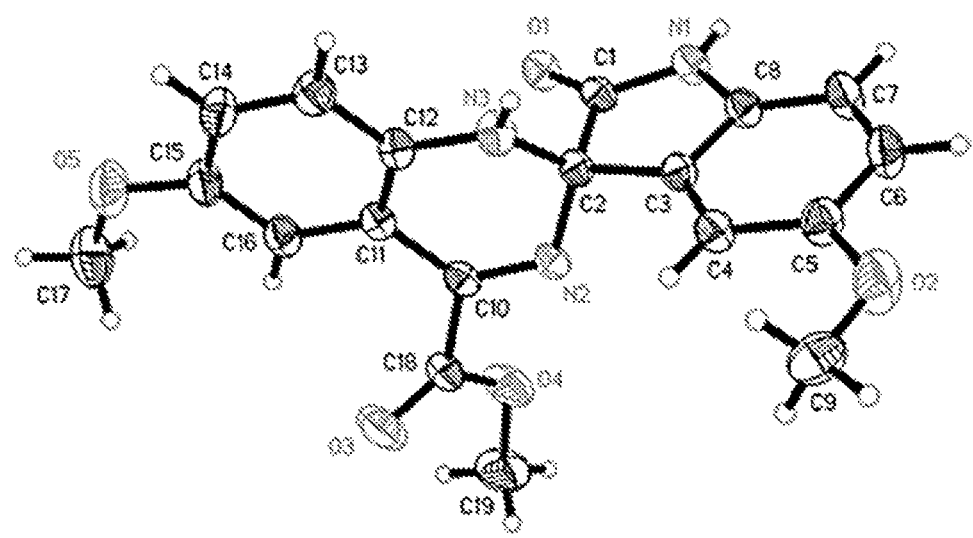
FIG. 1 is an X-ray diffraction analysis chart of Compound I.
Figure 2:
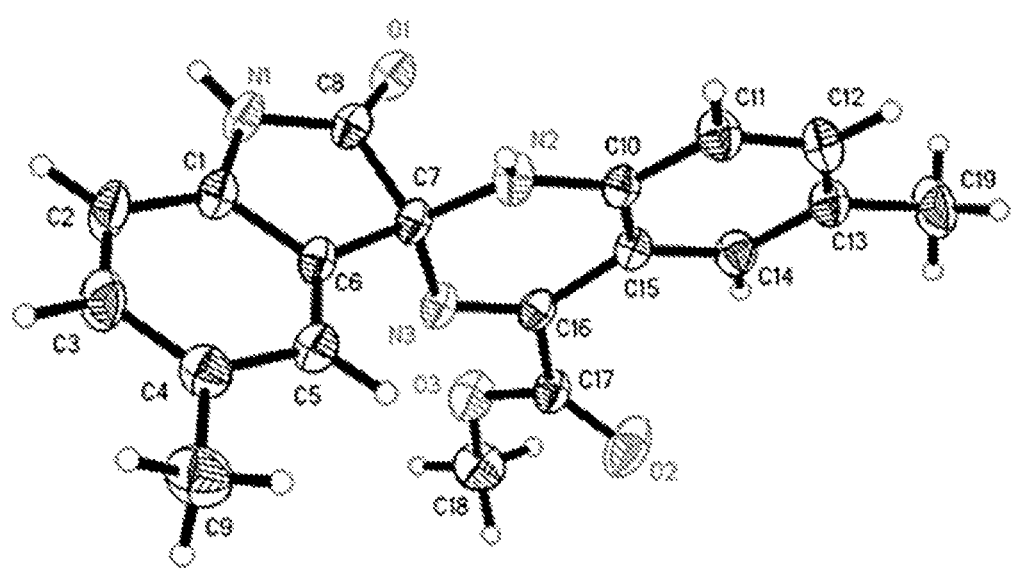
FIG. 2 is an X-ray diffraction analysis chart of Compound II.

To further illustrate the present application, experiments detailing 5-alkylquinazoline derivatives, a method of preparing the same, and a method of using the same are described below. It should be noted that the following examples are intended to describe and not to limit the present application

Example 1

Preparation of Chiral Palladium Complex (1) Preparation of [1,4-(4R)-diisopropyl-2-oxazolinyl] benzene 1.4054 g (10.64 mmol) of anhydrous $ZnCl_2$, 40 mL of chlorobenzene, 5.0236 g (39.2 mmol) of 1,4-dicyanobenzene, 16.2075 g of L-valinol were added in a 100 mL two-neck flask under an anhydrous and oxygen-free condition. A resulting mixture was refluxed at a high temperature for 60 hrs. The reaction was stopped, and then a solvent was removed under a reduced pressure to obtain a residue. After that, the residue was dissolved in water and extracted with $CHCl_3$ (20 mL×2). An organic phase was dried by anhydrous sodium sulfate, rotatory filtration was then performed to remove the solvent, and a crude product was performed with column chromatography with petroleum ether/dichloromethane (4:1) to obtain a light green viscous liquid with a yield of 52%. An obtained white crystal has a melting point of 48-50° C., $[a]^5_D$=+111.9° (c=0.429, $CHCl_3$); $^1H$ NMR (500 MHz, $CDCl_3$, 27° C.), δ(ppm)=7.97 (s, 4H), 4.39-4.43 (t, 3.18 Hz, 1H), 4.09-4.15 (m, 2H), 1.85-1.86 (m, 1H), (d, J=6.24 Hz, 6H), 0.86-0.96 (d, J=6.24 Hz, 6H). $^{13}C$ NMR 18.13, 19.03, 32.85, 70.26, 72.76, 128.10, 128.16, 130.32, 162.82. IR:3273, 2976, 2960, 2932, 2889, 2869, 1643, 1512, 1469, 1408, 1382, 1366, 1350, 1320, 1296, 1276, 1214, 1180, 1108, 1077, 1047, 1014, 971, 955, 900, 891, 838, 726, 698, 675, 659, 540. HRMS (EI): m/z (%): calcd for $C_{18}H_{24}N_2O_2$: 300.1838; found: 300.1833.

(2) Preparation of bis{[1,4-(4S)-diisopropyl-2-oxazolinylbenzene]palladium chloride} complex 1.5603 g (4.92 mmol) of palladium chloride, 1.0435 g (3.48 mmol) of 1,4-(4R)-diisopropyl-2-oxazolinylbenzene, and 30 mL of chlorobenzene were added to a 100 mL two-neck flask under an anhydrous and oxygen-free condition. A resulting mixture was refluxed at a high temperature for 48 hrs. The reaction was then stopped, and a solvent was removed under a reduced pressure. A resulting residue chloroform and ethanol were dissolved and naturally volatized to obtain a crystal of a reddish-brown complex, with a yield of 92%. m.p.:>200° C., $[a]^5_D$=+512.8° (c 0.0564, $CH_3OH$); $^1H$ NMR (600 MHz, $CDCl_3$), δ' ppm 8.81 (s, 8H, ArH), 4.61-4.63 (m, 4H, CH×4), 4.53 (t, J=9.6 Hz, 4H, CH×4), 4.44 (t, J=8.5 Hz, 4H, CH×4), 3.07-3.10 (m, 4H), 1.18 and 1.15 (dd, J=6.7, 7.2 Hz, 24H, CH3×4); $^{13}C$ NMR (150 MHz, $CDCl_3$) ppm 166.8, 130.1 (×2), 129.3, 72.0, 69.1, 30.7, 19.0, 15.6; $v_{max}(cm^{-1})$ 3487, 3049, 2957, 2929, 2872, 1642, 1609, 1572, 1509, 1480, 1464, 1416, 1379, 1331, 1288, 1246, 1178, 1141, 1123, 1099, 1045, 1018, 959, 933, 899, 854, 804, 770, 722, 693, 438.

Elemental Analysis:

$C_{36}H_{48}N_4Cl_4O_4Pd_2$: Test value: C 45.26%, H 5.06%, and N 5.86%; and theoretical value: C 45.32%, H5.24%, and N 5.48%.

Example 2

Preparation of Compound I 0.8847 g of 5-methoxyisatin, 2.6963 g of ammonium formate, and 100 mL of anhydrous methanol were added in a 250 mL round-bottomed flask, heated and stirred for 48 hrs. Then, reaction was stopped, and a rotary filtration was performed to obtain 1.1820 g of a crude filter residue. The crude filter residue was then performed with column chromatography (petroleum ether/dichloromethane: 1/1) to obtain a crystalline compound having a yield of 60%, a melting point of 232-234° C. ERMS ($C_{19}H_{17}N_3O_5$, m/e): a theoretical value of 367.1168, and a measured value of 367.1083. $^1H$ NMR (600 MHz, $CDCl_3$), δppm 10.0 (s, 1H), 6.90-6.92 (m, 2H), 6.85-6.87 (m, 3H), 6.76 (d, J=8.2 Hz, 1H), 6.55 (d, J=8.7 Hz, 1H), 3.87 (s, 3H), 3.73 (d, J=7.3 Hz, 6H); $^{13}C$ NMR (150 MHz, $CDCl_3$) δppm 175.4, 164.9 (×2), 158.8, 155.6, 151.3, 140.3, 134.4, 134.3, 121.9, 115.5, 115.4, 112.7, 111.7, 111.3, 111.1, 56.0 (×2), 53.0; IR spectrum data: (KBr; v, $cm^{-1}$): 3199, 2952, 2837, 1694, 1621, 1489, 1470, 1435, 1360, 1277, 899, 1202, 1159, 1114, 1084, 1024, 987, 956, 895, 874, 874, 816, 770, 710, 680, 650, 575, 534.

Example 3

Preparation of Compound II 0.8256 g of 5-methylisatin, 2.6963 g of ammonium formate and 100 mL of anhydrous methanol were added in a 250 mL round-bottomed flask, heated and stirred for refluxing for 48 hrs. Then, reaction was stopped, and a rotary filtration was performed to obtain 1.6033 g of a crude filter residue. The crude filter residue was then performed with column chromatography (petroleum ether/dichloromethane: 1/1) to obtain 0.8365 g of a crystalline compound having a yield of 62 wt. %, a melting point of >250° C. ERMS ($C_{19}H_{17}N_3O_3$, m/e): theoretical value: 335.1270; measured value: 335.1310; $^1H$ NMR (600 MHz, $CDCl_3$), δ ppm 8.05 (s, 1H), 7.13 (s, 1H), 7.08 (s, 1H), 7.01, 7.03 (dd, J=8.1 Hz, 7.7 Hz, 1H), 6.86 (s, 1H), 6.77 (d, J=7.8 Hz, 1H), 3.86 (s, 3H), 2.24 (s, 3H), 2.20 (s, 3H); $^{13}C$ NMR (150 MHz, $CDCl_3$) δppm 175.3, 164.6, 163.1, 158.6, 143.3, 138.0, 134.8, 133.0, 131.3, 130.2, 126.5, 125.6, 125.0, 113.8, 111.6, 110.0, 52.3, 20.7, 20.2; IR spectrum data: (KBr; v, $cm^{-1}$): 3182, 2952, 2920, 2853, 1696, 1623, 1574, 1489, 1456, 1377, 1348, 1310, 1226, 1170, 1030, 812, 654, 591, 548.

| Crystal data of compound I | |
|---|---|
| Empirical formula | C19H17N3O5 |
| Molecular weight | 367.35 |
| Temperature | 293(2) K |
| wavelength | 0.71073 Å |
| Crystal system, space group | Monoclinic, P21/n |
| Unit cell dimensions | a =9.9987(13) Å alpha = 90 deg. |
| | b =5.3433(7) Å beta = 92.743(5) deg. |
| | c =33.030(6) Å gamma = 90 deg. |
| volume | 1762.7(4) Å$^3$ |
| charge density | 4, 1.384 Mg/m$^3$ |
| Absorption correction parameter | 0.102 mm$^{-1}$ |
| Number of electrons in a unit cell | 768 |
| Crystal size | 0.120 × 0.100 × 0.060 mm |
| Theta range | 2.689 to 25.500 |
| Collection range of HKL's indicator | −10 <= h <= 12, −5 <= k < 6, −39 <= l <= 30 |

-continued

| Crystal data of compound I | |
|---|---|
| Reflections collected/unique | 7881/3272 [R (int) = 0.0360] |
| Completeness to theta =30.5 | 99.3% |
| Absorption correction method | Multi-layer scanning |
| Maximum and minimum transmittance | 0.7456 and 0.6857 |
| Refinement method | Full-matrix least-square on F$^2$ |
| Data number/restraint number/ parameter number | 3272/0/256 |
| Refinement method | 1.044 |
| Uniformity factor of diffraction point | R$_1$ = 0.0531, wR$_2$ = 0.1172 |
| Observable diffraction fit factor | R$_1$ = 0.1023, wR$_2$ = 0.1454 |
| Largest peak and hole on the difference Fourier diagram | 0.242 and −0.185 e. Å$^{-3}$ |

| Typical bond length data of crystal | |
|---|---|
| O(1)-C(1) | 1.231(3) |
| O(2)-C(5) | 1.373(3) |
| O(2)-C(9) | 1.398(4) |
| O(3)-C(18) | 1.201(3) |
| O(4)-C(18) | 1.307(3) |
| O(4)-C(19) | 1.449(3) |
| O(5)-C(15) | 1.382(3) |
| O(5)-C(17) | 1.391(4) |
| N(1)-C(1) | 1.333(3) |
| N(1)-C(8) | 1.417(3) |
| N(1)-H(1) | 0.87(3) |
| N(2)-C(10) | 1.284(3) |
| N(2)-C(2) | 1.465(3) |
| N(3)-C(12) | 1.377(3) |
| N(3)-C(2) | 1.435(3) |
| N(3)-H(3) | 0.83(3) |
| C(1)-C(2) | 1.571(3) |
| C(2)-C(3) | 1.516(3) |
| C(3)-C(4) | 1.377(3) |
| C(3)-C(8) | 1.381(3) |
| C(4)-C(5) | 1.388(4) |
| C(4)-H(4) | 0.9300 |
| C(5)-C(6) | 1.379(4) |
| C(6)-C(7) | 1.383(4) |
| C(6)-H(6) | 0.9300 |
| C(7)-C(8) | 1.367(4) |
| C(7)-H(7) | 0.9300 |
| C(9)-H(9A) | 0.9600 |
| C(9)-H(9B) | 0.9600 |
| C(9)-H(9C) | 0.9600 |
| C(10)-C(11) | 1.458(4) |
| C(10)-C(18) | 1.510(4) |
| C(11)-C(12) | 1.395(4) |
| C(11)-C(16) | 1.403(4) |
| C(12)-C(13) | 1.458(4) |
| C(13)-C(14) | 1.373(4) |
| C(13)-H(13) | 0.9300 |
| C(14)-C(15) | 1.385(4) |
| C(14)-H(14) | 0.9300 |
| C(15)-C(16) | 1.370(4) |
| C(16)-H(16) | 0.9300 |
| C(17)-H(17A) | 0.9600 |
| C(17)-H(17B) | 0.9600 |
| C(17)-H(17C) | 0.9600 |
| C(19)-H(19A) | 0.9600 |
| C(19)-H(19B) | 0.9600 |
| C(19)-H(19C) | 0.9600 |

| Bond angle data of crystal | |
|---|---|
| C(5)-O(2)-C(9) | 119.8(2) |
| C(18)-O(4)-C(19) | 117.9(3) |
| C(15)-O(5)-C(17) | 118.0(3) |
| C(1)-N(1)-C(8) | 112.0(2) |
| C(1)-N(1)-H(1) | 125(2) |
| C(8)-N(1)-H(1) | 122(2) |
| C(10)-N(2)-C(2) | 117.4(2) |
| C(12)-N(3)-C(2) | 120.9(2) |
| C(12)-N(3)-H(3) | 119.6(19) |
| C(2)-N(3)-H(3) | 119.5(19) |
| O(1)-C(1)-N(1) | 126.4(2) |
| O(1)-C(1)-C(2) | 125.4(2) |
| N(1)-C(1)-C(2) | 108.2(2) |
| N(3)-C(2)-N(2) | 112.7(2) |
| N(3)-C(2)-C(3) | 112.2(2) |
| N(2)-C(2)-C(3) | 111.92(19) |
| N(3)-C(2)-C(1) | 112.6(2) |
| N(2)-C(2)-C(1) | 105.68(18) |
| C(3)-C(2)-C(1) | 100.97(19) |
| C(4)-C(3)-C(8) | 120.7(2) |
| C(4)-C(3)-C(2) | 130.2(2) |
| C(8)-C(3)-C(2) | 109.1(2) |
| C(3)-C(4)-C(5) | 117.7(2) |
| C(3)-C(4)-H(4) | 121.2 |
| C(5)-C(4)-H(4) | 121.2 |
| O(2)-C(5)-C(6) | 114.6(3) |
| O(2)-C(5)-C(4) | 124.3(3) |
| C(6)-C(5)-C(4) | 121.1(3) |
| C(5)-C(6)-C(7) | 121.0(2) |
| C(5)-C(6)-H(6) | 119.5 |
| C(7)-C(6)-H(6) | 119.5 |
| C(8)-C(7)-C(6) | 117.5(3) |
| C(8)-C(7)-H(7) | 121.2 |
| C(6)-C(7)-H(7) | 121.2 |
| C(7)-C(8)-C(3) | 122.0(2) |
| C(7)-C(8)-N(1) | 128.3(2) |
| C(3)-C(8)-N(1) | 109.7(2) |
| O(2)-C(9)-H(9A) | 109.5 |
| O(2)-C(9)-H(9B) | 109.5 |
| H(9A)-C(9)-H(9B) | 109.5 |
| O(2)-C(9)-H(9C) | 109.5 |
| H(9A)-C(9)-H(9C) | 109.5 |
| H(9B)-C(9)-H(9C) | 109.5 |
| N(2)-C(10)-C(11) | 125.7(2) |
| N(2)-C(10)-C(18) | 114.4(2) |
| C(11)-C(10)-C(18) | 119.5(2) |
| C(12)-C(11)-C(16) | 120.0(3) |
| C(12)-C(11)-C(10) | 115.2(2) |
| C(16)-C(11)-C(10) | 124.6(2) |
| N(3)-C(12)-C(11) | 118.8(2) |
| N(3)-C(12)-C(13) | 121.7(2) |
| C(11)-C(12)-C(13) | 119.5(2) |
| C(14)-C(13)-C(12) | 119.4(3) |
| C(14)-C(13)-H(13) | 120.3 |
| C(12)-C(13)-H(13) | 120.3 |
| C(13)-C(14)-C(15) | 121.3(3) |
| C(13)-C(14)-H(14) | 119.3 |
| C(15)-C(14)-H(14) | 119.3 |
| C(16)-C(15)-O(5) | 125.7(3) |
| C(16)-C(15)-C(14) | 120.0(3) |
| O(5)-C(15)-(14) | 114.3(3) |
| C(15)-C(16)-C(11) | 119.7(3) |
| C(15)-C(16)-H(16) | 120.2 |
| C(11)-C(16)-H(16) | 120.2 |
| O(5)-C(17)-H(17A) | 109.5 |
| O(5)-C(17)-H(17B) | 109.5 |
| H(17A)-C(17)-H(17B) | 109.5 |
| O(5)-C(17)-H(17C) | 109.5 |
| H(17A)-C(17)-H(17C) | 109.5 |
| H(17B)-C(17)-H(17C) | 109.5 |
| O(3)-C(18)-O(4) | 123.5(3) |
| O(3)-C(18)-C(10) | 123.5(3) |
| O(4)-C(18)-C(10) | 112.9(2) |
| O(4)-C(19)-H(19A) | 109.5 |
| O(4)-C(19)-H(19B) | 109.5 |
| H(19A)-C(19)-H(19B) | 109.5 |
| O(4)-C(19)-H(19C) | 109.5 |
| H(19A)-C(19)-H(19C) | 109.5 |
| H(19B) C(19)-H(19C) | 109.5 |

| Crystal data of compound II | |
|---|---|
| Empirical formula | C19H17N3O3 |
| Molecular weight | 335.35 |
| Temperature | 293(2) K |
| Wavelength | 0.71073 Å |
| Crystal system, space group | triclinic, P21/c |
| Unit cell dimensions | a = 5.4404(2) Å alpha = 90 deg. |
| | b= 14.7573(5) Å beta = 91.5240(10) deg. |
| | c = 20.4239(7) Å gamma = 90 deg. |
| Volume | 1639.17 (10) Å$^3$ |
| Charge density | 4, 1.359 Mg/m$^3$ |
| Absorption correction parameter | 0.094 mm$^{-1}$ |
| Number of electrons in a unit cell | 704 |
| Crystal size | 0.190 × 0.120 × 0.090 mm |
| Theta range | 2.761 to 25.999 |
| Collection range of | −6 <= h <= 6, −18 <= k < 18, |
| HKL's indicator | −25 <= 1 <= 21 |
| Reflections collected/unique | 16418/3225 [R (int)=0.0400] |
| Completeness to theta = 30.5 | 99.8% |
| Absorption correction method | Multi-layer scanning |
| Maximum and minimum transmittance | 0.7456 and 0.6487 |
| Refinement method | Full-matrix least-square on F$^2$ |
| Data number/restraint number/parameter number | 3225/0/237 |
| Refinement method | 1.075 |
| Uniformity factor of diffraction point | $R_1$ =0.0546, $wR_2$ =0.1454 |
| Observable diffraction fit factor | $R_1$ =0.0742, $wR_2$ =0.1621 |
| Largest peak and hole on the difference Fourier diagram | 0.372 and −0.284 e.Å$^{-3}$ |

| Typical bond length data of crystal | |
|---|---|
| O(1)-C(8) | 1.220(3) |
| O(2)-C(17) | 1.198(3) |
| O(3)-C(17) | 1.304(3) |
| O(3)-C(18) | 1.442(3) |
| N(1)-C(8) | 1.342(3) |
| N(1)-C(1) | 1.406(3) |
| N(1)-H(1) | 0.82(3) |
| N(2)-C(10) | 1.365(3) |
| N(2)-C(7) | 1.439(3) |
| N(2)-H(2) | 0.78(3) |
| N(3)-C(16) | 1.282(3) |
| N(3)-C(7) | 1.467(3) |
| C(1)-C(2) | 1.379(3) |
| C(1)-C(6) | 1.388(3) |
| C(2)-C(3) | 1.379(4) |
| C(2)-H(2A) | 0.9300 |
| C(3)-C(4) | 1.384(4) |
| C(3)-H(3) | 0.9300 |
| C(4)-C(5) | 1.398(3) |
| C(4)-C(9) | 1.503(4) |
| C(5)-C(6) | 1.375(3) |
| C(5)-H(5) | 0.9300 |
| C(6)-C(7) | 1.511(3) |
| C(7)-C(8) | 1.572(3) |
| C(9)-H(9A) | 0.9600 |
| C(9)-H(9B) | 0.9600 |
| C(9)-H(9C) | 0.9600 |
| C(10)-C(11) | 1.388(3) |
| C(10)-C(15) | 1.406(3) |
| C(11)-C(12) | 1.381(3) |
| C(11)-H(11) | 0.9300 |
| C(12)-C(13) | 1.387(4) |
| C(12)-H(12) | 0.9300 |
| C(13)-C(14) | 1.381(4) |
| C(13)-C(19) | 1.507(3) |
| C(14)-C(15) | 1.401(3) |
| C(14)-H(14) | 0.9300 |
| C(15)-C(16) | 1.459(3) |
| C(16)-C(17) | 1.513(3) |
| C(18)-H(18A) | 0.9600 |
| C(18)-H(18B) | 0.9600 |

| Typical bond length data of crystal | |
|---|---|
| C(18)-H(18C) | 0.9600 |
| C(19)-H(19A) | 0.9600 |
| C(19)-H(19B) | 0.9600 |
| C(19)-H(19C) | 0.9600 |

| Bond angle data of crystal | |
|---|---|
| C(16)-O(4)-C(17) | 115.7(3) |
| C(17)-O(3)-C(18) | 116.9(2) |
| C(8)-N(1)-C(1) | 112.1(2) |
| C(8)-N(1)-H(1) | 123.7(18) |
| C(1)-N(1)-H(1) | 114.1(18) |
| C(10)-N(2)-C(7) | 122.96(18) |
| C(10)-N(2)-H(2) | 120(2) |
| C(7)-N(2)-H(2) | 116(2) |
| C(16)-N(3)-C(7) | 118.29(18) |
| C(2)-C(1)-C(6) | 121.5(2) |
| C(2)-C(1)-N(1) | 128.9(2) |
| C(6)-C(1)-N(1) | 109.65(19) |
| C(1)-C(2)-C(3) | 117.2(2) |
| C(1)-C(2)-H(2A) | 121.4 |
| C(3)-C(2)-H(2A) | 121.4 |
| C(2)-C(3)-C(4) | 123.1(2) |
| C(2)-C(4)-H(3) | 118.5 |
| C(4)-C(3)-H(3) | 118.5 |
| C(3)-C(4)-C(5) | 118.4(2) |
| C(3)-C(4)-C(9) | 121.5(2) |
| C(5)-C(4)-C(9) | 120.1(2) |
| C(6)-C(5)-C(4) | 119.5(2) |
| C(6)-C(5)-H(5) | 120.2 |
| C(4)-C(5)-H(5) | 120.2 |
| C(5)-C(6)-C(1) | 120.3(2) |
| C(5)-C(6)-C(7) | 130.4(2) |
| C(1)-C(6)-C(7) | 109.25(19) |
| N(2)-C(7)-N(3) | 114.15(16) |
| N(2)-C(7) -C(6) | 111.37(17) |
| N(3)-C(7) -C(7) | 112.47(18) |
| N(2)-C(7)-C(8) | 112.30(19) |
| N(3)-C(7)-C(8) | 104.60(16) |
| C(6)-C(7)-C(8) | 101.00(16) |
| O(1)-C(8)-N(1) | 126.8(2) |
| O(1)-C(8)-C(7) | 125.20(19) |
| N(1)-C(8)-C(7) | 107.98(19) |
| C(4)-C (9)-H(9A) | 109.5 |
| C(4)-C(9)-H(9B) | 109.5 |
| H(9A)-C(9)-H(9B) | 109.5 |
| C(4)-C(9)-H(9C) | 109.5 |
| H(9A)-C(9)-H(9C) | 109.5 |
| H(9B)-C(9)-H(9C) | 109.5 |
| N(2)-C(10)-C(11) | 121.3(2) |
| N(2)-C(10)-C(15) | 119.13(19) |
| C(11)-C(10)-C(15) | 119.5(2) |
| C(12)-C(11)-C(10) | 119.6(2) |
| C(12)-C(11)-H(11) | 120.2 |
| C(10)-C(11)-H(11) | 120.2 |
| C(11)-C(12)-C(13) | 122.3(2) |
| C(11)-C(12)-H(12) | 118.8 |
| C(13)-C(12)-H(12) | 118.8 |
| C(14)-C(13)-C(12) | 117.7(2) |
| C(14)-C(13)-C(19) | 121.0(2) |
| C(12)-C(13)-C(19) | 121.3(2) |
| C(13)-C(14)-C(15) | 121.7(2) |
| C(13)-C(14)-H(14) | 119.1 |
| C(15)-C(14)-H(14) | 119.1 |
| C(14)-C(15)-C(10) | 119.0(2) |
| C(14)-C(15)-C(16) | 125.2(2) |
| C(10)-C(15)-C(16) | 115.54(18) |
| N(3)-C(16)-C(15) | 125.83(19) |
| N(3)-C(16)-(17) | 114.92(19) |
| C(15)-C(16)-C(17) | 118.95(18) |
| O(2)-C(17)-O(3) | 123.2(2) |
| O(2)-C(17)-C(16) | 123.9(2) |
| O(3)-C(17)-C(16) | 112.84(19) |
| O(3)-C(18)-H(18A) | 109.5 |

-continued

| Bond angle data of crystal | |
|---|---|
| O(3)-C(18)-H(18B) | 109.5 |
| H(18A)-C(18)-H(18B) | 109.5 |
| O(3)-C(18)-H(18C) | 109.5 |
| H(18A)-C(18)-H(18C) | 109.5 |
| H(18B)-C(18)-H(18C) | 109.5 |
| C(13)-C(19)-H(19A) | 109.5 |
| C(13)-C(19)-H(19B) | 109.5 |
| H(19A)-C(19)-H(19B) | 109.5 |
| C(13)-C(19)-H(19C) | 109.5 |
| H(19A)-C(19)-H(19C) | 109.5 |
| H(19B)-C(19)-H(19C) | 109.5 |

Example 4

Use of Henry Reaction

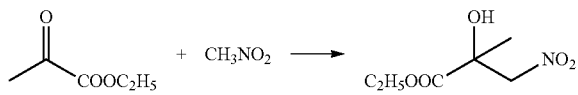

0.05 mmol of compound I and compound II were placed in a 25 mL flask, then 1 mL of tetrahydrofuran, 0.3 mL of nitromethane, and 0.5 mmol of ethyl pyruvate were added in sequence. A resulting mixture were stirred for reaction for 20 hrs at room temperature. After that, samples of the compound I and the compound II were collected respectively for detection by $^1$HNMR, which indicated that conversion rates of the compound I and the compound II are respectively 90.7% and 89.0%. $^1$H NMR (600 MHz, CDCl$_3$): δ) 4.86 (d, J=13.8 Hz, 1H), 4.58 (d, J=13.8 Hz, 1H), 4.34 (m,2H), 3.85 (s,1H), 1.46 (s,3H), 1.33 (t, J=7.2 Hz, 3H). $^{13}$C NMR (150 MHz, CDCl$_3$): δ=173.4, 80.9, 72.4, 63.0, 23.8, 13.9.

Example 5

Study on the Anticancer Activity of Compound II

The compound (II) synthesized according to the target design of the present invention shows certain inhibitory activity in the MCF test of breast cancer cells (ED50<10.0 μg/mL). Therefore, the compounds of the present application are expected to be useful in the treatment of various cancers, such as cervical cancer.

Test results of some anti-cancer activities of the compounds of the present invention are shown in Table 1:

TABLE 1

| Anti-cancer activity data (IC$_{50}$ value) of compound (II) | | |
|---|---|---|
| | Cell line Cervical cancer | |
| sample | Mean value | Standard deviation |
| Quinazoline derivative (II) | 90.13 | ±1.83 |

Unless otherwise indicated, the numerical ranges involved in the present application include the end values. While particular embodiments of the present application have been shown and described, it will be obvious to those skilled in the art that changes and modifications may be made without departing from the present application in its broader aspects, and therefore, the aim in the appended claims is to cover all such changes and modifications as fall within the true spirit and scope of the present application.

What is claimed is:

1. A 5-methoxyquinazoline derivative compound I, having a structure represented by formula I and prepared by 5-methoxyisatin and ammonium formate in an anhydrous methanol solution.

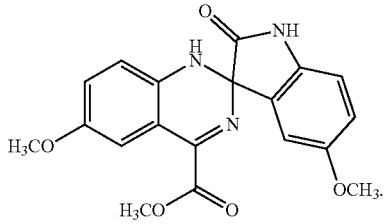

Formula I

2. A 5-methylquinazoline derivative compound II, having a structure represented by formula II and prepared by 5-methylisatin and ammonium formate in an anhydrous methanol solution.

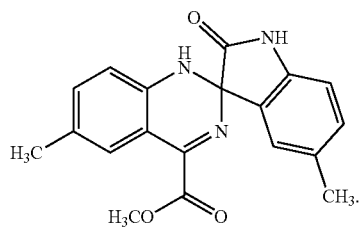

Formula II

3. The 5-methoxyquinazoline derivative compound I according to claim 1, prepared into a form of a crystal, wherein
when being diffracted with a MoKα ray, which is monochromated by a graphite monochromator and has a wavelength of π=0.71073 Å, in an ω-θ scanning mode on an Oxford X-ray single crystal diffractometer at a temperature of 293(2)K, the crystal of the 5-methoxyquinazoline derivative compound I belongs to a monoclinic system, P21/n, and has unit cell dimensions as follows: a=9.9987(13) Å, alpha=90 deg; b=5.3433(7) Å, beta=92.743(5) deg; and c=33.030(6) Å, gamma=90 deg.

4. The 5-methylquinazoline derivative compound II according to claim 2, prepared into a form of a crystal, wherein
when being diffracted with a MoKα ray, which is monochromated by a graphite monochromator and has a wavelength of λ=0.71073 Å, in an ω-θ scanning mode on an Oxford X-ray single crystal diffractometer at a temperature of 293(2)K, the crystal of the 5-methoxyquinazoline derivative compound II belongs to a triclinic system, P21/c, and has unit cell dimensions as follows: a=5.4404(2) Å, alpha=90 deg; b=14.7573(5) Å, beta=91.5240(10) deg; and c=20.4239(7) Å, gamma=90 deg.

5. A method for preparing crystals of a 5-methoxyquinazoline derivative compound I, having a structure represented by formula I, Formula I

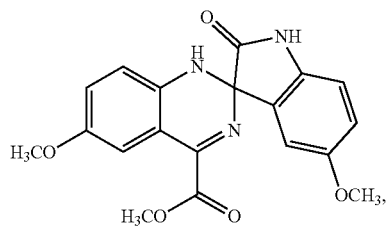

and a 5-methylquinazoline derivative compound II, having a structure represented by formula II;

Formula II

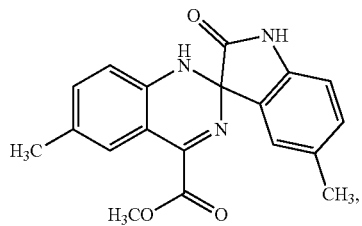

the method comprising:
  a synthesis step, comprising:
    adding 0.8847 g of 5-methoxyisatin, 0.8256 g of 5-methylisatin, 2.6963 g of ammonium formate, and 100 mL of anhydrous methanol in a 250 mL round-bottomed flask; heating and stirring a resulting mixture for refluxing for 48 hrs, stopping reaction, and performing rotary filtration and obtaining a crude filter residue; and
  a separation step, comprising:
    performing column chromatography on the crude filter residue using dichloromethane and anhydrous methanol at a volume ratio of 1:1, and respectively obtaining the crystal of 5-methoxyquinazoline derivative compound I and the crystal of 5-methylquinazoline derivative compound II.

6. A method of using the 5-methoxyquinazoline derivative compound I of claim 1 in a Henry reaction of ethyl pyruvate, having a conversion rate of 90.7 wt. %.

7. A method of the 5-methylquinazoline derivative compound II of claim 2, in a Henry reaction of ethyl pyruvate, wherein a conversion rate of the 5-methylquinazoline derivative compound II has a conversion rate of 89.0 wt. %, or as an anti-cancer agent, wherein the 5-methylquinazoline derivative compound II shows a certain anti-cancer effect in anti-cancer activity, and has an $IC_{50}$ value of 90.13±1.83.

* * * * *